US012324703B2

(12) United States Patent
Yoshida (10) Patent No.: US 12,324,703 B2
(45) Date of Patent: Jun. 10, 2025

(54) ULTRASOUND PROBE, ULTRASOUND TRANSDUCER UNIT, AND ULTRASOUND ENDOSCOPE

(71) Applicant: OLYMPUS CORPORATION, Tokyo (JP)

(72) Inventor: Satoshi Yoshida, Kawagoe (JP)

(73) Assignee: OLYMPUS CORPORATION, Tokyo (JP)

( * ) Notice: Subject to any disclaimer, the term of this patent is extended or adjusted under 35 U.S.C. 154(b) by 52 days.

(21) Appl. No.: 18/219,797

(22) Filed: Jul. 10, 2023

(65) Prior Publication Data

US 2023/0346342 A1 Nov. 2, 2023

Related U.S. Application Data (63) Continuation of application No. PCT/JP2021/014815, filed on Apr. 7, 2021.

(51) Int. Cl.
*A61B 8/12* (2006.01)
*A61B 8/00* (2006.01)

(52) U.S. Cl.
CPC ............... *A61B 8/12* (2013.01); *A61B 8/445* (2013.01); *A61B 8/4477* (2013.01)

(58) Field of Classification Search
CPC ......... A61B 8/12; A61B 8/445; A61B 8/4477; A61B 8/4483; A61B 8/4488; A61B 8/4494; B06B 1/0633; H04R 17/00
See application file for complete search history.

(56) References Cited

U.S. PATENT DOCUMENTS

| | | | |
|---|---|---|---|
| 2015/0112201 A1* | 4/2015 | Nakanishi | A61B 8/4411 600/472 |
| 2015/0245815 A1 | 9/2015 | Wakabayashi | |
| 2017/0128043 A1* | 5/2017 | Morimoto | A61B 1/0011 |
| 2019/0029646 A1* | 1/2019 | Yamamoto | B06B 1/0633 |
| 2019/0350555 A1* | 11/2019 | Wakabayashi | A61B 8/4494 |

FOREIGN PATENT DOCUMENTS

| | | |
|---|---|---|
| JP | 5889121 B2 | 3/2016 |
| JP | 2017-225621 A | 12/2017 |
| WO | 2015/011969 A1 | 1/2015 |

OTHER PUBLICATIONS

International Search Report dated Jun. 22, 2021 received in PCT/JP2021/014815.

* cited by examiner

*Primary Examiner* — Adil Partap S Virk
(74) *Attorney, Agent, or Firm* — Scully, Scott, Murphy & Presser, P.C.

(57) ABSTRACT

An ultrasound probe includes: a transducer array in which a plurality of transducers configured to transmit and receive ultrasonic waves are arrayed with longitudinal directions of the transducers aligned; and a pair of housings each having a plate shape, the housings being configured to sandwich the transducers, the housings including a first conductive portion provided on a first face positioned on a side of each of the transducers, an insulating portion provided on an outer edge portion of a second face that is positioned on an opposite side of the first face, a second conductive portion provided on the second face, and a third conductive portion electrically connecting the first conductive portion and the second conductive portion.

20 Claims, 12 Drawing Sheets

FIG.20

ULTRASOUND PROBE, ULTRASOUND TRANSDUCER UNIT, AND ULTRASOUND ENDOSCOPE

CROSS-REFERENCE TO RELATED APPLICATION

This application is a continuation of International Application No. PCT/JP2021/014815, filed on Apr. 7, 2021, the entire contents of which are incorporated herein by reference.

BACKGROUND

1. Technical Field

The present disclosure relates to an ultrasound probe, an ultrasound transducer unit, and an ultrasound endoscope.

2. Related Art

In the related art, an ultrasound probe including a transducer array in which a plurality of transducers for transmitting and receiving ultrasonic waves is arrayed with their longitudinal directions aligned and a housing for holding the transducer array is known (see, for example, Japanese Patent No. 5889121 A).

In an ultrasound probe, a structure is known in which a part of a housing has an electrical conductivity, and an outer periphery of the housing is covered with an insulating acoustic lens. According to this structure, since the part of the housing has an electrical conductivity, electromagnetic noise can be reduced. In addition, since the outer periphery of the housing is covered with the acoustic lens, a current applied to a transducer can be prevented from leaking to the outside via the housing.

SUMMARY

In some embodiments, an ultrasound probe includes: a transducer array in which a plurality of transducers configured to transmit and receive ultrasonic waves are arrayed with longitudinal directions of the transducers aligned; and a pair of housings each having a plate shape, the housings being configured to sandwich the transducers, the housings including a first conductive portion having an electrical conductivity, the first conductive portion being provided on a first face positioned on a side of each of the transducers, an insulating portion having an insulating property, the insulating portion being provided on an outer edge portion of a second face that is positioned on an opposite side of the first face, the edge portion including a region obtained by projecting each of the transducers on the second face in a longitudinal direction of each of the transducers, a second conductive portion having an electrical conductivity, the second conductive portion being provided on the second face, and a third conductive portion electrically connecting the first conductive portion and the second conductive portion.

In some embodiments, an ultrasound transducer unit includes: a transducer array in which a plurality of transducers configured to transmit and receive ultrasonic waves are arrayed with longitudinal directions of the transducers aligned; and a pair of housings each having a plate shape, the housings being configured to sandwich the transducers, the housings including a first conductive portion having an electrical conductivity, the first conductive portion being provided on a first face positioned on a side of each of the transducers, an insulating portion having an insulating property, the insulating portion being provided on an outer edge portion of a second face that is positioned on an opposite side of the first face, the edge portion including a region obtained by projecting each of the transducers on the second face in a longitudinal direction of each of the transducers, a second conductive portion having an electrical conductivity, the second conductive portion being provided on the second face, and a third conductive portion electrically connecting the first conductive portion and the second conductive portion.

In some embodiments, an ultrasound endoscope includes: an ultrasound probe including a transducer array in which a plurality of transducers configured to transmit and receive ultrasonic waves are arrayed with longitudinal directions of the transducers aligned, and a pair of housings each having a plate shape, the housings being configured to sandwich the transducers, the housings including a first conductive portion having an electrical conductivity, the first conductive portion being provided on a first face positioned on a side of each of the transducers, an insulating portion having an insulating property, the insulating portion being provided on an outer edge portion of a second face that is positioned on an opposite side of the first face, the edge portion including a region obtained by projecting each of the transducers on the second face in a longitudinal direction of each of the transducers, a second conductive portion having an electrical conductivity, the second conductive portion being provided on the second face, and a third conductive portion electrically connecting the first conductive portion and the second conductive portion; and an insertion portion having a distal end provided with the ultrasound probe, the insertion portion being configured to be inserted into a subject.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, embodiments of an ultrasound probe, an ultrasound transducer unit, and an ultrasound endoscope according to the disclosure will be described with reference to the drawings. Note that the disclosure is not limited by these embodiments. The disclosure is applicable to ultrasound probes, ultrasound transducer units, and ultrasound endoscopes in general.

Incidentally, in the description of the drawings, the same or corresponding elements are denoted by the same symbol as appropriate. In addition, it should be noted that the drawings are schematic and that a dimensional relationship of elements, a ratio of elements, and the like may be different from reality. Some parts may have a different dimensional relationship or different ratios between drawings.

First Embodiment

Schematic Configuration of Endoscope System

Figure 1:
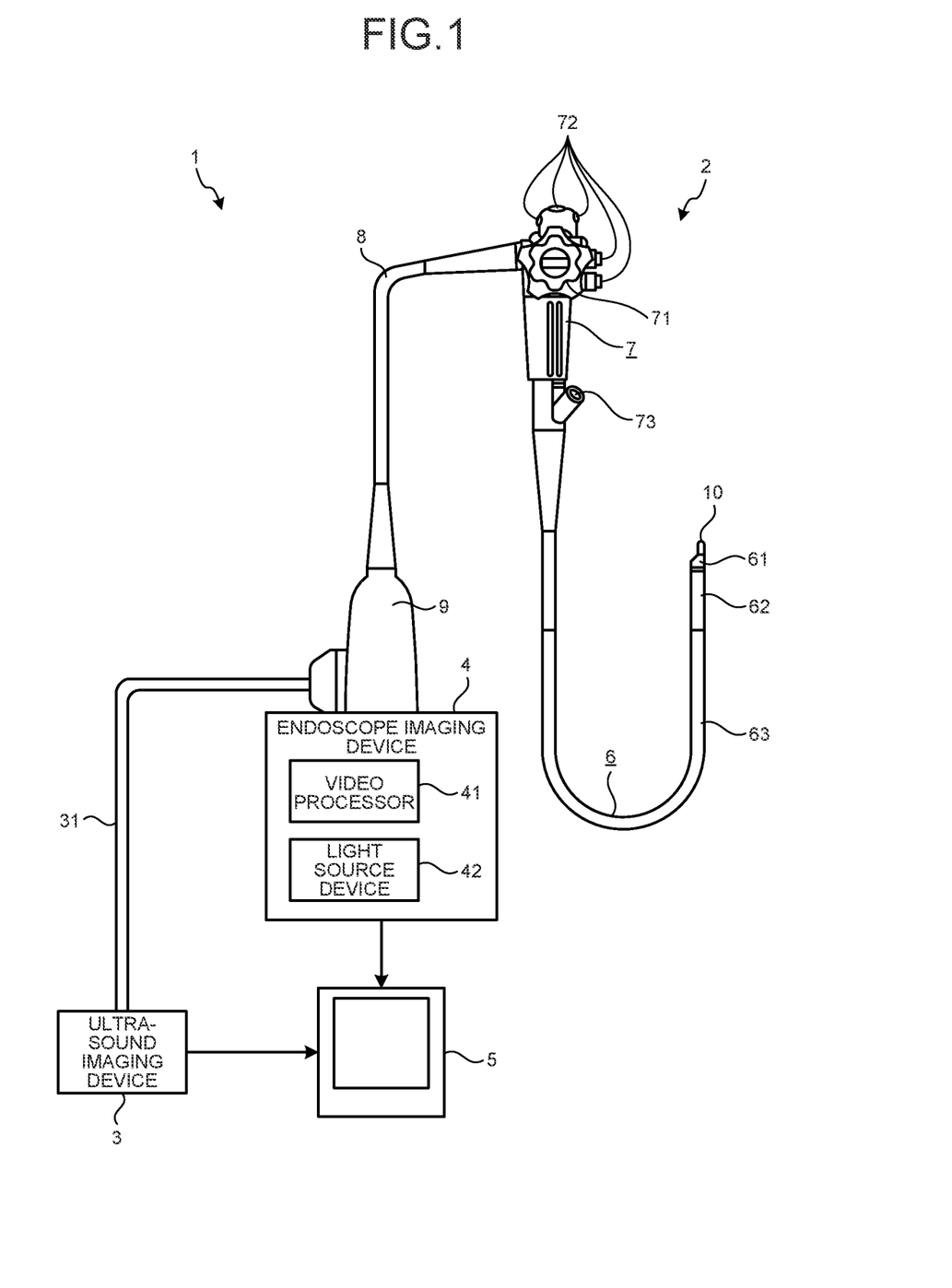
FIG. 1 is a diagram illustrating an endoscope system including an ultrasound probe according to a first embodiment.

FIG. 1 is a diagram illustrating an endoscope system including an ultrasound probe according to a first embodiment. An endoscope system 1 performs ultrasound diagnosis and treatment on the inside of a subject such as a person by using an ultrasound endoscope. As illustrated in FIG. 1, the endoscope system 1 includes an ultrasound endoscope 2, an ultrasound imaging device 3, an endoscope imaging device 4, and a display device 5.

A part of the ultrasound endoscope 2 can be inserted into the subject and has a function of transmitting an ultrasound pulse (acoustic pulse) toward a body wall inside the subject and receiving an ultrasound echo reflected by the subject and a function of capturing an image of the inside of the subject and outputting an image signal. Note that a detailed structure of the ultrasound endoscope 2 will be described later.

The ultrasound imaging device 3 is electrically connected to the ultrasound endoscope 2 via an ultrasound cable 31 and outputs a pulse signal to the ultrasound endoscope 2 via the ultrasound cable 31 and receives an echo signal from the ultrasound endoscope 2. The ultrasound imaging device 3 further performs predetermined processing on the echo signal to generate an ultrasound image.

An endoscope connector 9 of the ultrasound endoscope 2 is detachably connected to the endoscope imaging device 4. As illustrated in FIG. 1, the endoscope imaging device 4 includes a video processor 41 and a light source device 42.

The video processor 41 receives an image signal from the ultrasound endoscope 2 via the endoscope connector 9. The video processor 41 further performs predetermined processing on the image signal to generate an endoscopic image.

The light source device 42 supplies illumination light for illuminating the inside of the subject to the ultrasound endoscope 2 via the endoscope connector 9.

The display device 5 includes liquid crystal, organic electro luminescence (EL), a cathode ray tube (CRT), or a projector and displays the ultrasound image generated by the ultrasound imaging device 3, the endoscopic image generated by the endoscope imaging device 4, or the like.

Structure of Ultrasound Endoscope

Next, the structure of the ultrasound endoscope 2 will be described. As illustrated in FIG. 1, the ultrasound endoscope 2 includes an insertion portion 6, an operating portion 7, a universal cord 8, and the endoscope connector 9.

Figure 2:
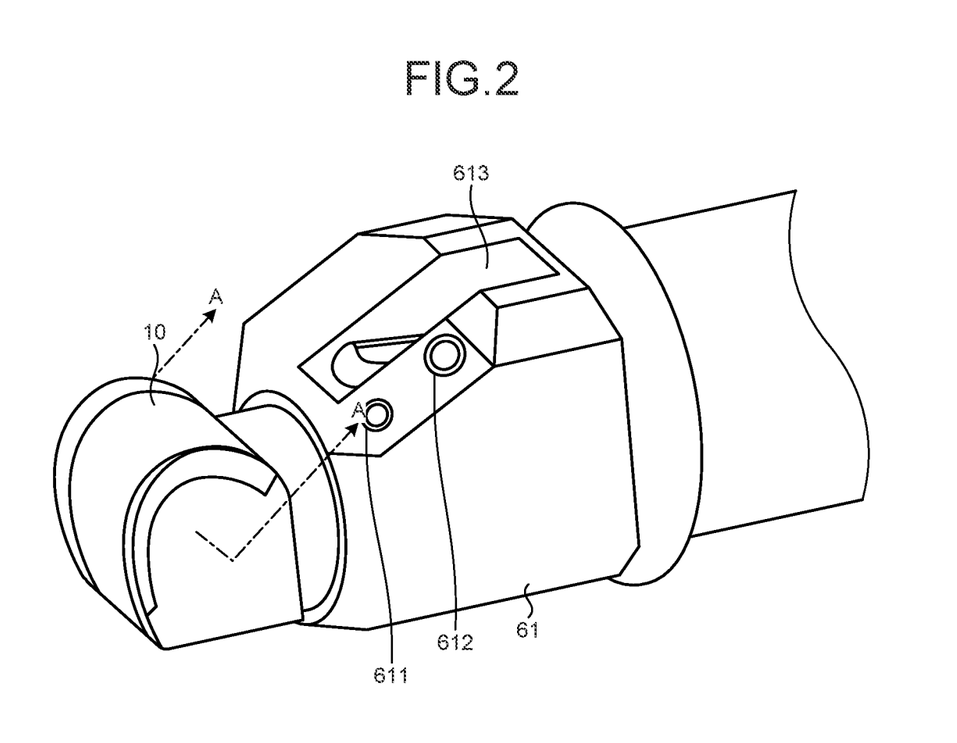
FIG. 2 is a perspective view illustrating a distal end of an insertion portion.

FIG. 2 is a perspective view illustrating a distal end of the insertion portion. Note that, in the following description of the structure of the insertion portion 6, a distal end side of the insertion portion 6 (distal end side in an insertion direction into the subject) is simply referred to as "distal end side", and a proximal end side of the insertion portion 6 (side away from a distal end of the insertion portion 6) is referred to as "proximal end side".

The insertion portion 6 is a portion to be inserted inside the subject. As illustrated in FIG. 1 of FIG. 2, the insertion portion 6 includes an ultrasound probe 10 included on the distal end side, a rigid portion 61 connected to the proximal end side of the ultrasound probe 10, a bendable portion 62 which is bendable and is connected to the proximal end side of the rigid portion 61, and a flexible tube 63 (FIG. 1) which is flexible and is connected to the proximal end side of the bendable portion 62.

Note that, inside the insertion portion 6, the operating portion 7, the universal cord 8, and the endoscope connector 9, a light guide that transmits illumination light supplied from the light source device 42, a transducer cable that transmits a pulse signal or an echo signal, and a signal cable that transmits an image signal are routed, and a pipeline for circulating a fluid is included.

The rigid portion 61 is a rigid member made of a resin material and others. As illustrated in FIG. 2, in the distal end of the rigid portion 61, an illumination portion 611 that irradiates the inside of the subject with illumination light, an imaging portion 612 that captures an image of the inside of the subject, and a treatment instrument channel 613 that causes a treatment instrument to protrude from the distal end of the insertion portion 6 are arranged.

The illumination portion 611 includes a light guide that transmits the illumination light output from the light source device 42 to the distal end of the insertion portion 6 and an illumination lens that irradiates the inside of the subject with the illumination light emitted from an emission end of the light guide.

The imaging portion 612 includes an objective optical system that condenses light (subject image) emitted to the inside of the subject and reflected by the inside of the subject and an imaging element that captures a subject image obtained by condensing the light by the objective optical system. Then, an image signal captured by the imaging element is transmitted to the endoscope imaging device 4 (video processor 41) via the signal cable.

The treatment instrument channel 613 is a passage through which a treatment instrument such as a puncture needle inserted inside the insertion portion 6 is caused to protrude to the outside.

The operating portion 7 is connected to the proximal end side of the insertion portion 6 and accepts various types of operation from a doctor or the like. As illustrated in FIG. 1, the operating portion 7 includes a bending knob 71 for bending operation of the bendable portion 62 and a plurality of operating members 72 for performing various types of operation.

In addition, the operating portion 7 includes a treatment instrument insertion port 73 (FIG. 1) which communicates with the treatment instrument channel 613 via a tube provided inside the bendable portion 62 and the flexible tube 63 and through which a treatment instrument is inserted.

The universal cord 8 extends from the operating portion 7 and in which a tube constituting parts of the light guide, the transducer cable, the signal cable, and the pipeline is disposed.

The endoscope connector 9 is provided at an end of the universal cord 8. The endoscope connector 9 is further connected with the ultrasound cable 31 and is connected to the video processor 41 and the light source device 42 by being inserted into the endoscope imaging device 4.

Structure of Ultrasound Transducer

Figure 3:
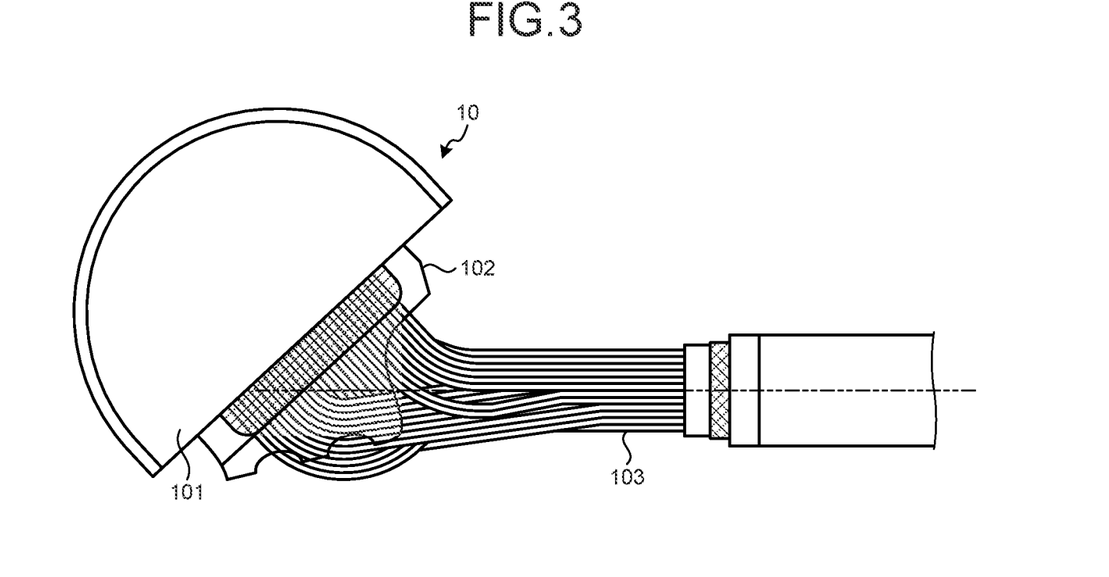
FIG. 3 is a schematic structure diagram of an ultrasound probe.

Next, the structure of the ultrasound probe 10 will be described. FIG. 3 is a schematic structure diagram of the ultrasound probe. As illustrated in FIG. 3, the ultrasound probe 10 has a convex-type ultrasound transducer unit and includes a pair of housings 101, a substrate 102 positioned between the housings 101, and a transducer cable 103 connected to the substrate 102.

Figure 4:
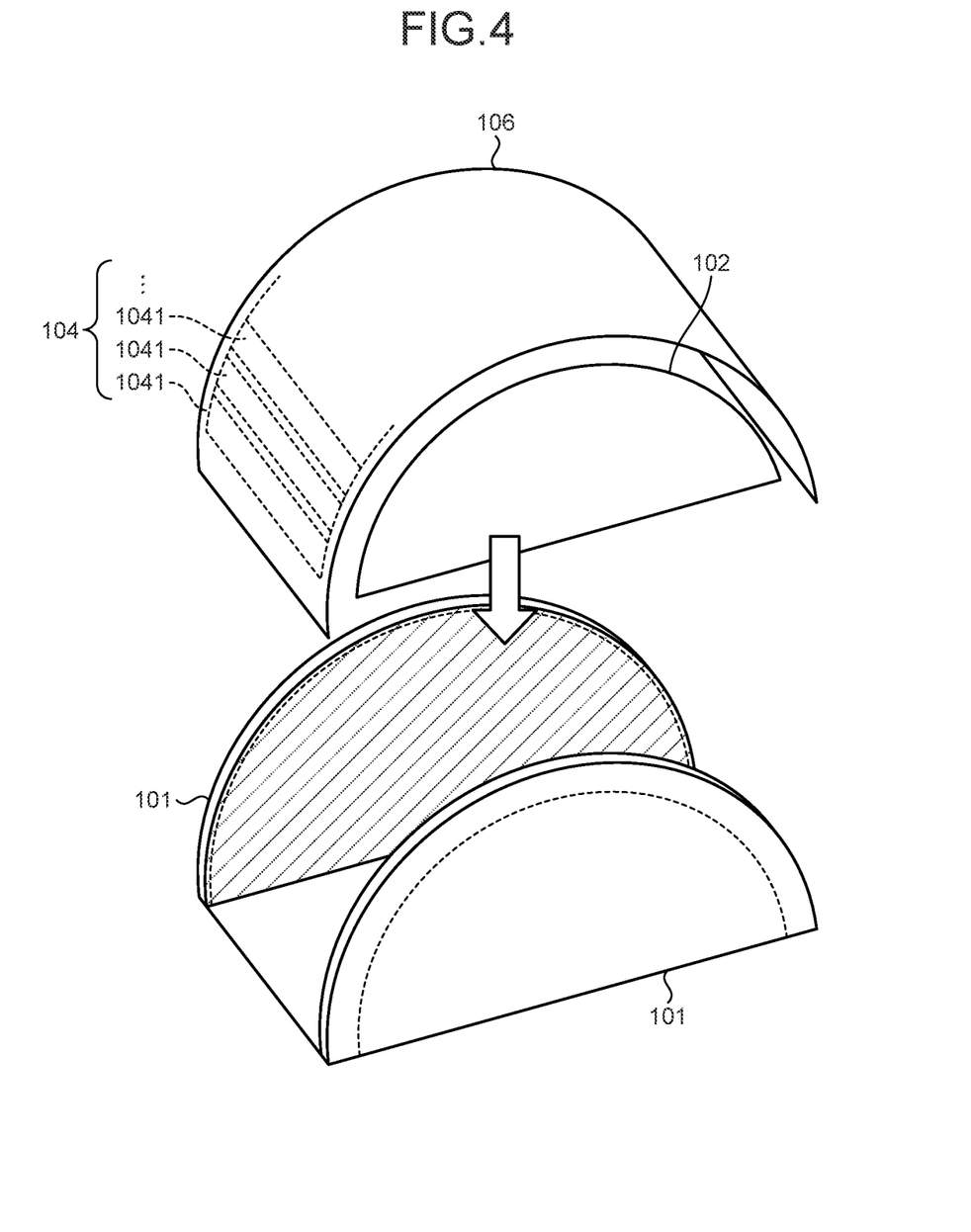
FIG. 4 is an exploded view of the ultrasound probe.

FIG. 4 is an exploded view of the ultrasound probe. As illustrated in FIG. 4, the ultrasound probe 10 includes a transducer array 104 including a plurality of transducers 1041 that are arranged between the housings 101 and that are arrayed in an arc shape.

Figure 5:
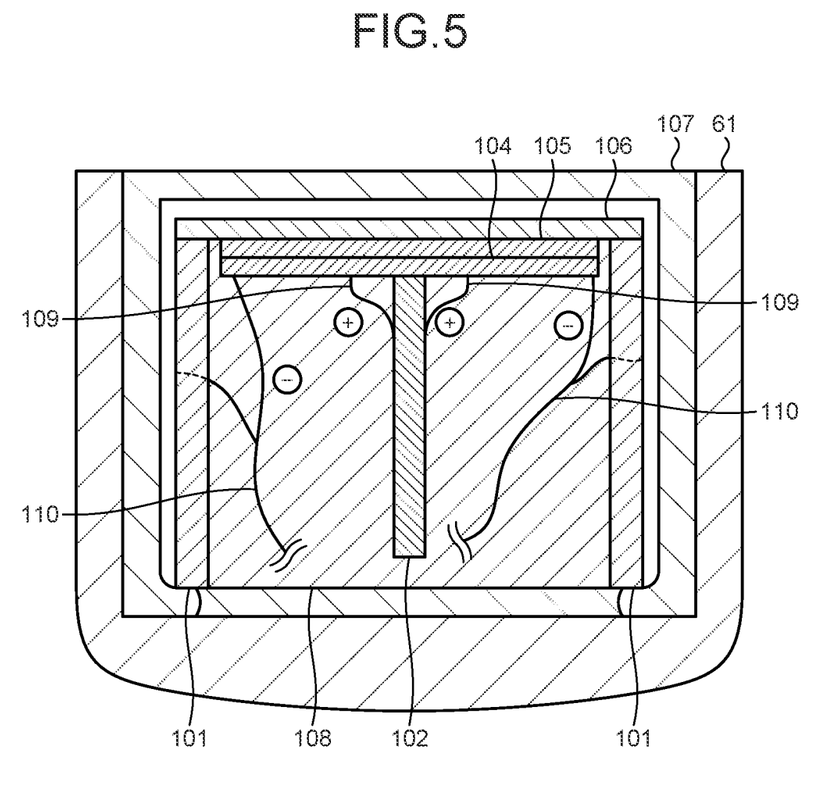
FIG. 5 is a cross-sectional view corresponding to line A-A in FIG. 2.

FIG. 5 is a cross-sectional view corresponding to line A-A in FIG. 2. As illustrated in FIG. 5, the ultrasound probe 10 includes an ultrasound transducer unit including the transducer array 104, a first acoustic matching layer 105 and a second acoustic matching layer 106 provided facing (opposed to) the transducer array 104, and the housings 101 holding the first acoustic matching layer 105 and the second acoustic matching layer 106, the substrate 102 electrically connected to the transducer array 104, the transducer cable 103 electrically connected to the substrate 102, an acoustic lens 107 covering an outer periphery of the ultrasound transducer unit, a backing material 108 filling the inside of the housings 101, and wiring 109 and 110 electrically connected to the individual transducers 1041, the ultrasound probe 10 accommodated in the rigid portion 61. Note that to provide the first acoustic matching layer 105 and the second acoustic matching layer 106 facing (opposed to) the transducer array 104 includes, for example, a mode in which the first acoustic matching layer 105 and the second acoustic matching layer 106 hold the transducer array 104. Also included are a mode in which the first acoustic matching layer 105 and the second acoustic matching layer 106 are placed in a state of being in contact with the transducer array 104 and a state in which the first acoustic matching layer 105 and the second acoustic matching layer 106 face the transducer array 104 via a liquid or gel, namely, states not limited to the state of being held.

The housings 101 hold both end sides in the longitudinal direction of the second acoustic matching layer 106 with the individual transducers 1041 interposed therebetween. The housings 101 is made of resin such as glass epoxy resin and has a pair of plate shapes. The housings 101 preferably holds both of the ends in the longitudinal direction of the second acoustic matching layer 106. Furthermore, for example, the width of the second acoustic matching layer 106 may be set slightly larger than the interval between the housings 101. In this case, the second acoustic matching layer 106 may be held by outer peripheries of the housings 101. A detailed structure of the housings 101 will be described later.

The substrate 102 is a flexible substrate and electrically connects the transducer cable 103 and each of the transducers 1041.

The transducer cable 103 transmits the pulse signal output from the ultrasound imaging device 3 to each of the transducers 1041 and transmits an echo signal output from each of the transducers 1041 to the ultrasound imaging device 3.

The transducer array 104 includes the plurality of transducers 1041 that transmits and receives ultrasonic waves. The transducers 1041 are arrayed along an arc with their longitudinal directions aligned.

Each of the transducers 1041 is formed of an elongated rectangular parallelepiped, and a pair of electrodes is formed on an outer face thereof. A transducer 1041 further converts a pulse signal input via the transducer cable 103 and a pair of electrodes into an ultrasound pulse and transmits the ultrasound pulse to the subject. The transducer 1041 also converts an ultrasound echo reflected by the subject into an electrical echo signal expressed by a voltage change and outputs the echo signal to the transducer cable 103 via the pair of electrodes. The transducers 1041 are formed using a PMN-PT single crystal, a PMN-PZT single crystal, a PZN-PT single crystal, a PIN-PZN-PT single crystal, or a relaxor-based material. Note that the PMN-PT single crystal is an abbreviation of a solid solution of lead-magnesium niobate and lead titanate. The PMN-PZT single crystal is an abbreviation of a solid solution of lead-magnesium niobate and lead zirconate titanate. The PZN-PT single crystal is an abbreviation of a solid solution of lead zinc-niobate and lead titanate. The PIN-PZN-PT single crystal is an abbreviation of a solid solution of lead indium niobate, lead zinc niobate, and lead titanate. The relaxor-based material is a generic term for three-component piezoelectric materials obtained by adding lead-based composite perovskite, which is a relaxor-based material, to lead zirconate titanate (PZT) for the purpose of increasing the piezoelectric constant and the dielectric constant. The lead-based composite perovskite is represented by $Pb(B1, B2)O_3$, where B1 is any one of magnesium, zinc, indium, or scandium, and B2 is any one of niobium, tantalum, or tungsten. These materials have an excellent piezoelectric effect. Therefore, even if the size is reduced, the value of the electrical impedance can be reduced, which is preferable from the viewpoint of impedance matching between a pair of electrodes.

The first acoustic matching layer 105 and the second acoustic matching layer 106 are positioned, with respect to the transducer array 104, in a direction in which each of the transducers 1041 transmits an ultrasonic wave. The second acoustic matching layer 106 forms a series along the array direction of the plurality of transducers 1041 and holds the individual transducers 1041. The first acoustic matching layer 105 and the second acoustic matching layer 106 match acoustic impedances between the transducer array 104 and an observation target in order to efficiently transmit sound (ultrasonic waves) between the transducer array 104 and the observation target. The first acoustic matching layer 105 and the second acoustic matching layer 106 are made of different materials. Note that, in the first embodiment, it is described on the premise that two acoustic matching layers (the first acoustic matching layer 105 and the second acoustic matching layer 106) are included, however, it is optional whether to provide no acoustic matching layers, a single acoustic matching layer, or three or more acoustic matching layers depending on the characteristics of the transducer array 104 and an observation target.

The acoustic lens 107 is formed using silicone, polymethylpentene, epoxy resin, polyetherimide, or the like, has one face having a convex or concave shape, has a function of narrowing down ultrasonic waves, and emits ultrasonic waves having passed through the acoustic matching layers to the outside or captures an ultrasound echo from the outside. The acoustic lens 107 can also be provided as desired, and the acoustic lens 107 may not be included.

The backing material 108 attenuates unnecessary ultrasound vibration generated by the operation of the transducers 1041. The backing material 108 is formed using a material having a high attenuation rate such as an epoxy resin in which a filler such as alumina or zirconia is dispersed or rubber in which the filler is dispersed. Note that the backing material 108 may not be provided depending on the characteristics of the transducer array 104 and the observation target.

The wiring 109 is electrically connected to a positive electrode of each of the transducers 1041. The wiring 110 is electrically connected to a negative electrode of each of the transducers 1041.

Structure of Housing

Next, the structure of the housing 101 will be described. In the following description, a first face of a housing 101 positioned on the individual transducers 1041 side is also referred to as an inner face, and a second face located on an opposite side of the first face is also referred to as an outer face.

Figure 6:
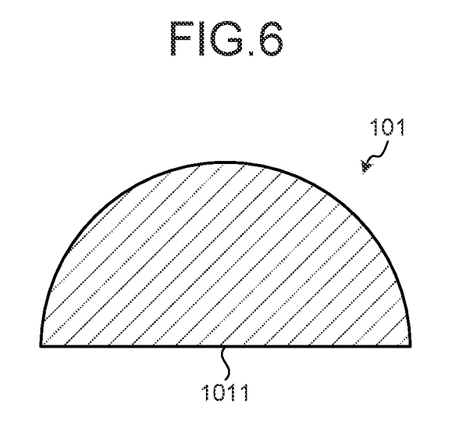
FIG. 6 is a diagram illustrating an inner face of a housing.

FIG. 6 is a diagram illustrating the inner face of the housing. As illustrated in FIG. 6, a housing 101 includes a conductive portion 1011 having an electrical conductivity, the conductive portion 1011 included over the entire inner face. The conductive portion 1011 may be provided by metal plating such as that of copper on the housing 101 made of an insulating member such as resin or may be provided by attaching a conductive sheet such as copper on the housing 101. In addition, the conductive portion 1011 may be provided by activating a part of the insulating material. Alternatively, an insulating portion 1012 may be provided on the conductive portion 1011 by oxidizing a part of the conductive material. Note that being conductive means that the electrical conductivity is high enough to drive the transducers 1041.

Figure 7:
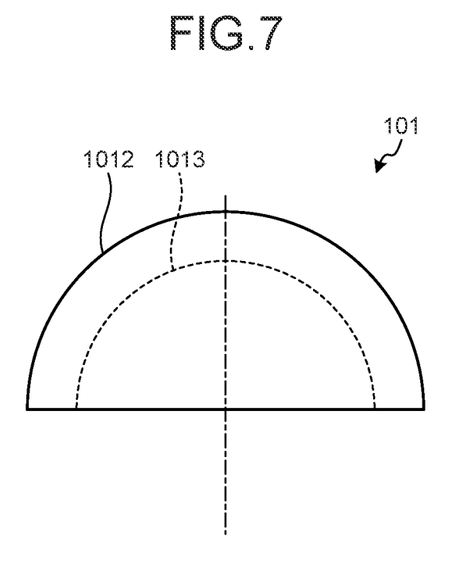
FIG. 7 is a diagram illustrating an outer face of the housing.

FIG. 7 is a diagram illustrating an outer face of a housing. As illustrated in FIG. 7, a housing 101 includes an insulating portion 1012 that has an insulating property and that is provided on the outer face. The insulating portion 1012 is provided at an outer edge portion including a region where the individual transducers 1041 are projected in the longitudinal direction. The term "having an insulating property" means that the electrical conductivity is low enough to reduce the electromagnetic noise.

According to the first embodiment described above, since the conductive portion 1011 is provided on the inner face of the housing 101, the electromagnetic noise can be reduced. Note that the electromagnetic noise is caused by electromagnetic waves generated by the ultrasound endoscope 2 such as the imaging portion 612, electromagnetic waves generated by the ultrasound imaging device 3, the endoscope imaging device 4, and the display device 5, and electromagnetic waves generated by various electric devices present around the endoscope system 1 such as other devices in the operating room, a fluorescent light, air conditioners, or others in the operating room.

Furthermore, since the insulating portion 1012 is provided on the outer edge portion of the outer face of the housing 101, the conductive portion of the housing 101 is not included at a position close to the outside, and thus even in a case where a large current flows due to lightning or the like or in a case where the acoustic lens 107 is damaged, it is possible to prevent the current from flowing through the subject, and thus, there is high safety. Note that, since the ultrasound probe 10 is housed in the rigid portion 61 (see FIG. 7), a current is prevented from flowing to the subject from portions other than the insulating portion 1012.

Incidentally, the conductive portion 1011 preferably includes a region where the individual transducers 1041 are projected in the longitudinal direction. With the conductive portion 1011 covers this region, the effect of reducing the electromagnetic noise can be enhanced.

In addition, the conductive portion 1011 is provided from the outer edge portion, including the region where the individual transducers 1041 are projected in the longitudinal direction, toward the center of the inner face and preferably has an area that is half or more of an area of the inner face. With the conductive portion 1011 having a sufficiently wide area, the effect of reducing the electromagnetic noise can be enhanced.

In addition, the housing 101 may include an insulating portion that has an insulating property and that is provided on the outer edge portion of the inner face. By making the outer edge portion of the inner face of the housing 101 insulating, the effect of preventing a current from flowing through the subject can be enhanced.

In addition, the housing 101 may include an insulating portion that has an insulating property and that is provided on a side face connecting the inner face and the outer face. By making the side face of the housing 101 insulating, the effect of preventing a current from flowing through the subject can be enhanced.

In addition, an insulating portion 1013 may be provided in a region inside the insulating portion 1012 on the outer face of the housing 101 to enhance the effect of preventing a current from flowing through the subject, or a conductive portion may be provided in this region to enhance the effect of reducing the electromagnetic noise.

First Modification

Figure 8:
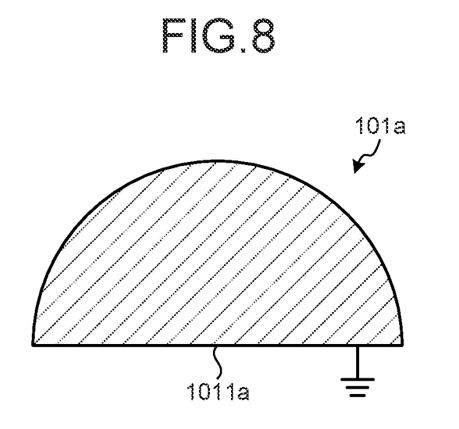
FIG. 8 is a diagram illustrating an inner face of a housing according to a first modification.

FIG. 8 is a diagram illustrating an inner face of a housing according to a first modification. As illustrated in FIG. 8, a housing 101a according to the first modification includes a conductive portion 1011a provided on an inner face, and a grounding wire is electrically connected to the conductive portion 1011a. Specifically, wiring 110 electrically connected to a negative electrode of each transducer 1041 is electrically connected to the conductive portion 1011a by soldering or the like. As a result, the effect of reducing the electromagnetic noise can be enhanced.

Second Modification

Figure 9:
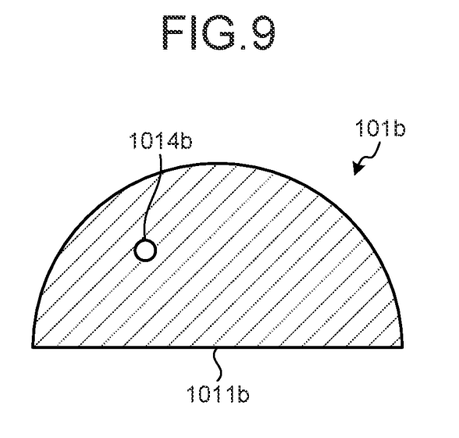
FIG. 9 is a diagram illustrating an inner face of a housing according to a second modification.

FIG. 9 is a diagram illustrating an inner face of a housing according to a second modification. As illustrated in FIG. 9, a through hole 1014b communicating from an inner face to an outer face is formed in a housing 101b according to the second modification. The housing 101b also includes a conductive portion that has an electrical conductivity and that is provided on the inner face of the through hole 1014b.

Figure 10:
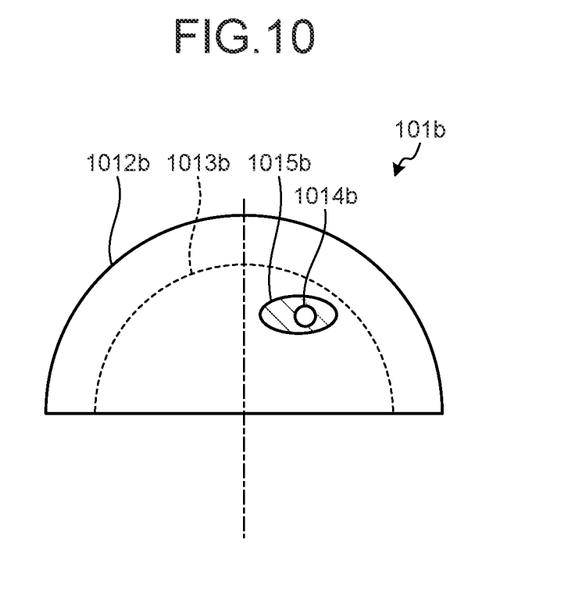
FIG. 10 is a diagram illustrating an outer face of the housing according to the second modification.

FIG. 10 is a diagram illustrating the outer face of the housing according to the second modification. As illustrated in FIG. 10, the housing 101b includes an elliptical conductive portion 1015b having an electrical conductivity, the conductive portion 1015b provided around the through hole 1014b on the outer face. The conductive portion 1015b on the outer face of the housing 101b is electrically connected with a conductive portion 1011b on the inner face via the conductive portion on the inner face of the through hole 1014b.

Furthermore, a grounding wire connected to a transducer 1041 is electrically connected to the conductive portion 1015*b*. As a result, the conductive portion 1011*b* on the inner face is grounded via the conductive portion 1015*b* and the conductive portion of the through hole 1014*b*, and thus the effect of reducing the electromagnetic noise can be enhanced. In addition, since it is only required to solder the grounding wire (wiring 110) to the conductive portion 1015*b* on the outer face, workability is better than a case where the grounding wire is soldered to the inner face. Furthermore, since the conductive portion 1015*b* is provided on the outer face, whether or not the housing 101*b* is grounded can be inspected from the outside of the housing 101*b* by a tester or the like, and thus workability is good.

Note that the conductive portion 1015*b* may have any shape as long as the grounding wire is easily soldered and may not be an ellipse.

Third Modification

Figure 11:
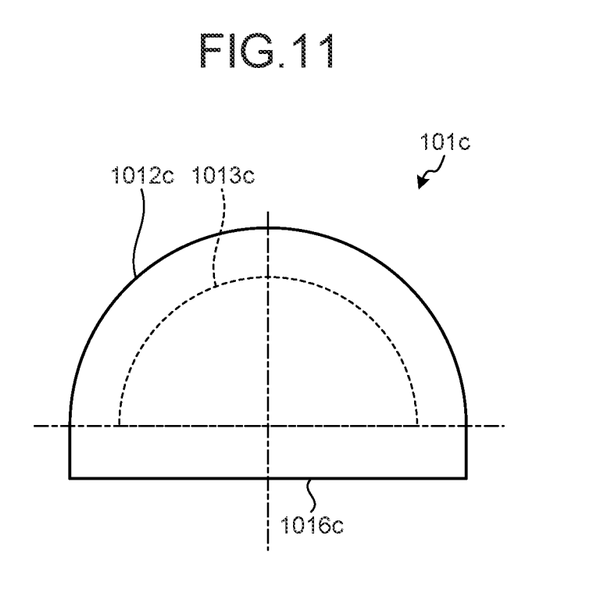
FIG. 11 is a diagram illustrating an outer face of a housing according to a third modification.

FIG. 11 is a diagram illustrating an outer face of a housing according to a third modification. As illustrated in FIG. 11, a housing 101*c* according to a third modification includes a semicircular portion (insulating portion 1012*c* and insulating portion 1013*c*) having a semicircular shape and an extension portion 1016*c* having a long side substantially coinciding with the diameter (long diameter) of the semicircular portion and extending to a side opposite to the arc of the semicircular portion. Note that the semicircular portion may have a shape obtained by cutting a part of an ellipse.

With the extension portion 1016*c*, the housing 101*c* and a transducer array 104 can be accurately aligned. Note that the extension portion 1016 *c* may be cut off after aligning the housing 101*c* and the transducer array 104 and fixing the housing 101*c* and the transducer array 104 with an adhesive agent or the like.

Second Embodiment

Figure 12:
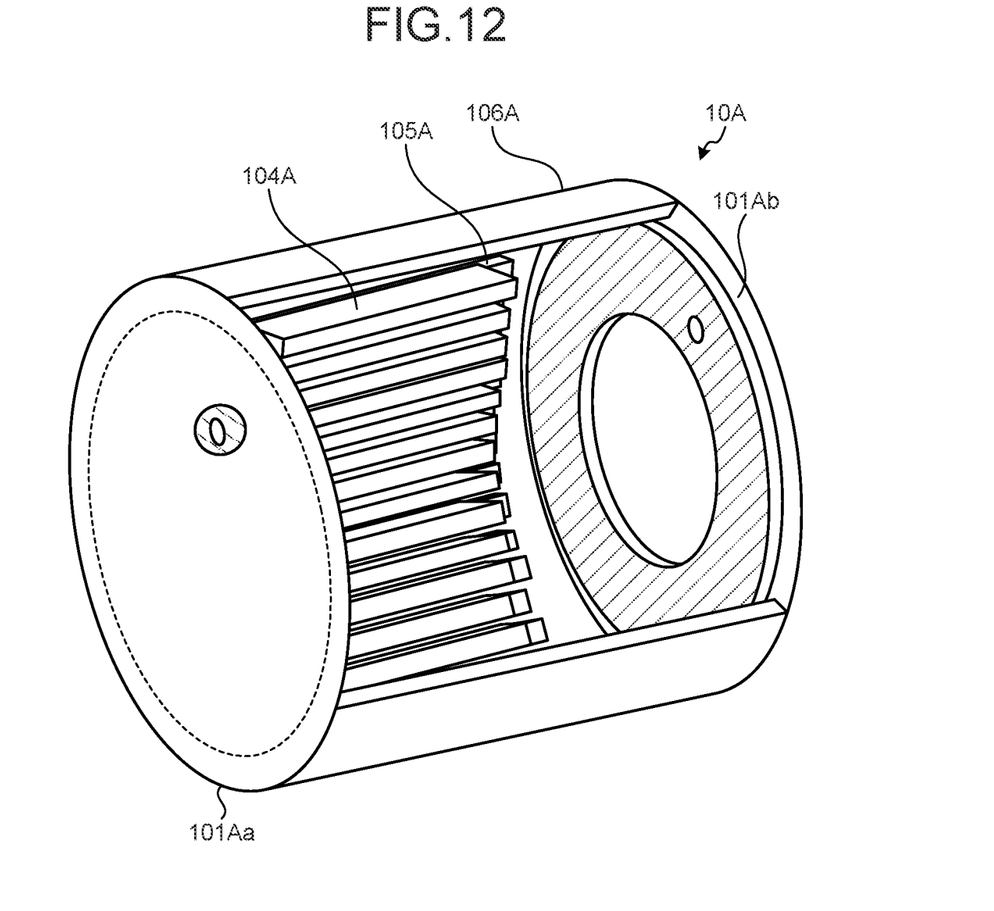
FIG. 12 is a schematic structure diagram of an ultrasound probe according to a second embodiment.

FIG. 12 is a schematic structure diagram of an ultrasound probe according to a second embodiment. FIG. 12 is a diagram in which a part of an ultrasound probe 10A, which is a radial-type ultrasound transducer, is cut out. The ultrasound probe 10A includes a pair of housings 101Aa and 101Ab, a transducer array 104A in which a plurality of transducers that transmits and receives ultrasonic waves is arrayed with their longitudinal directions aligned, and a first acoustic matching layer 105A and a second acoustic matching layer 106A that are positioned in a direction in which the individual transducers transmit ultrasonic waves, the first acoustic matching layer 105A and the second acoustic matching layer 106A facing (opposed to) the individual transducers.

Figure 13:
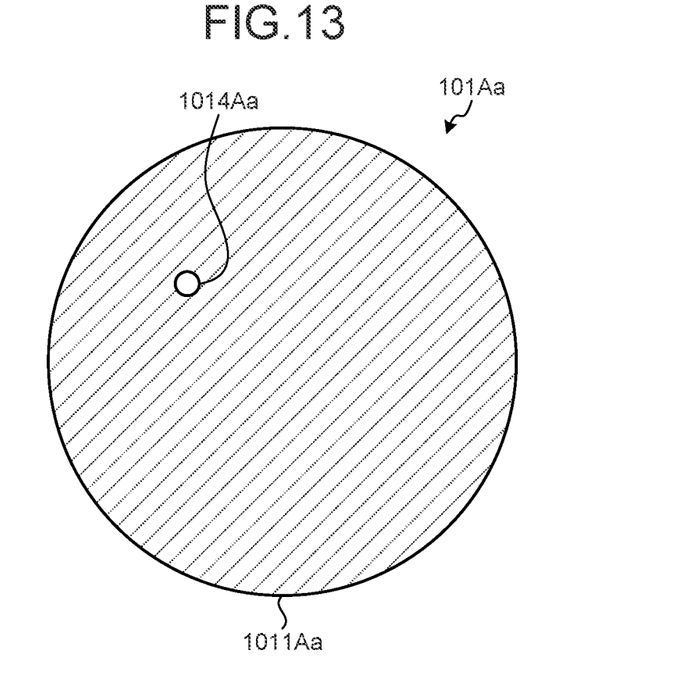
FIG. 13 is a diagram illustrating an inner face of a housing on a distal end side.

FIG. 13 is a diagram illustrating an inner face of a housing on the distal end side. As illustrated in FIG. 13, the housing 101Aa includes a conductive portion 1011Aa that has an electrical conductivity and that is provided over the entire inner face.

A through hole 1014Aa communicating from the inner face to the outer face is formed in the housing 101Aa. In addition, the housing 101Aa includes a conductive portion that has an electrical conductivity and that is provided on an inner face of the through hole 1014Aa.

Figure 14:
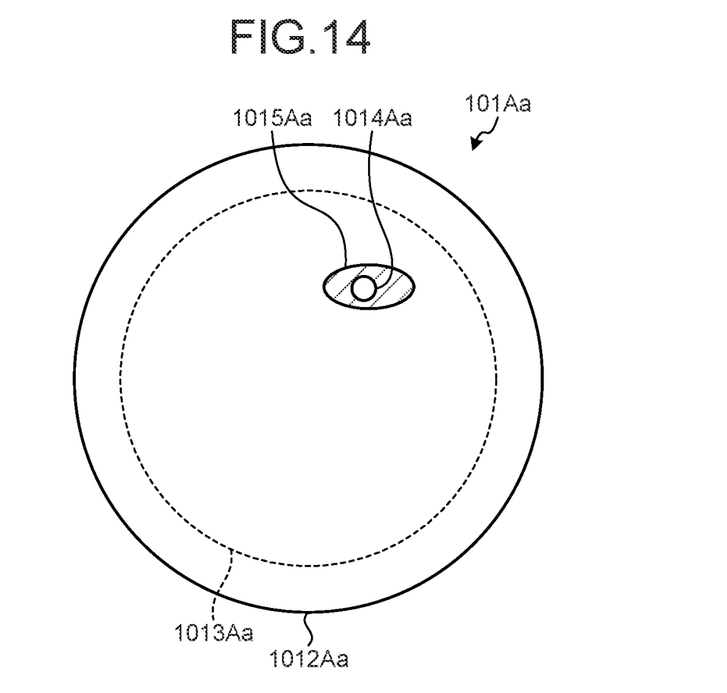
FIG. 14 is a diagram illustrating an outer face of the housing on the distal end side.

FIG. 14 is a diagram illustrating the outer face of the housing on the distal end side. As illustrated in FIG. 14, the housing 101Aa includes an insulating portion 1012Aa that has an insulating property and that is provided on the outer face. The insulating portion 1012Aa is provided at an outer edge portion including a region where the individual transducers are projected in the longitudinal direction. In addition, the housing 101Aa includes an elliptical conductive portion 1015Aa that has an electrical conductivity and that is provided around the through hole 1014Aa on the outer face.

Figure 15:
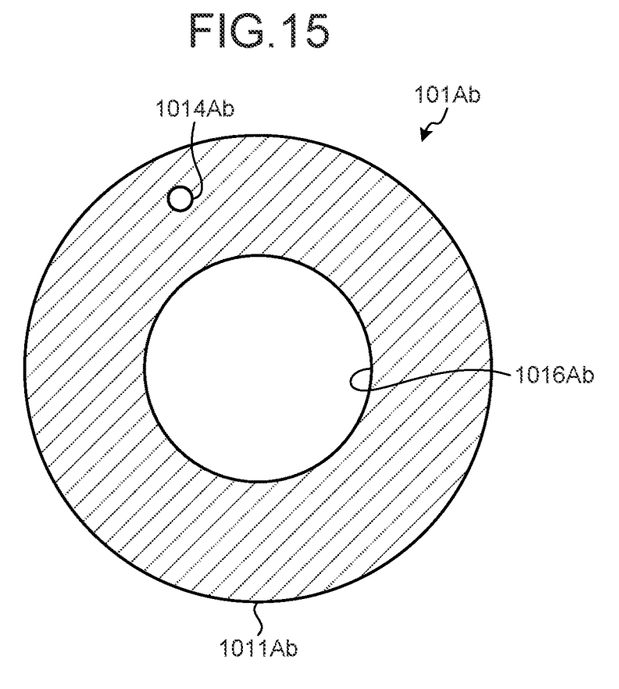
FIG. 15 is a diagram illustrating an inner face of the housing on a proximal end side.

FIG. 15 is a diagram illustrating an inner face of the housing on the proximal end side. As illustrated in FIG. 15, the housing 101Ab includes a conductive portion 1011Ab that has an electrical conductivity and that is provided over the entire inner face. A hole 1016Ab through which a transducer cable is inserted is formed at the center of the housing 101Ab.

In the housing 101Ab, a through hole 1014Ab communicating from the inner face to the outer face is formed. In addition, the housing 101Ab includes a conductive portion that has an electrical conductivity and that is provided on an inner face of the through hole 1014Ab.

Figure 16:
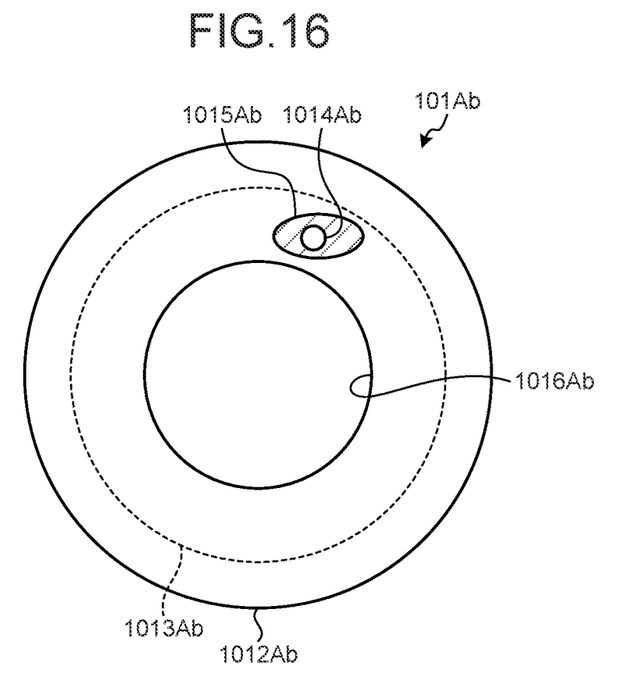
FIG. 16 is a diagram illustrating an outer face of the housing on the proximal end side.

FIG. 16 is a diagram illustrating the outer face of the housing on the proximal end side. As illustrated in FIG. 16, the housing 101Ab includes an insulating portion 1012Ab that has an insulating property and that is provided on the outer face. The insulating portion 1012Ab is provided at an outer edge portion including a region where the individual transducers are projected in the longitudinal direction. In addition, the housing 101Ab includes an elliptical conductive portion 1015Ab that has an electrical conductivity and that is provided around the through hole 1014Ab on the outer face.

According to the second embodiment described above, since the conductive portion 1011Aa and the conductive portion 1011Ab are provided on the inner faces of the housing 101Aa and the housing 101Ab, the electromagnetic noise can be reduced. Furthermore, since the insulating portion 1012Aa and the insulating portion 1012Ab are provided on the outer faces of the housing 101Aa and the housing 101Ab, even in a case where a large current flows due to lightning or the like, it is possible to prevent a current from flowing through a subject.

In addition, a grounding wire connected to the transducers is electrically connected to the conductive portion 1015Aa and the conductive portion 1015Ab. As a result, the conductive portion 1011Aa and the conductive portion 1011Ab on the inner face are grounded via the conductive portions of the through hole 1014Aa and the through hole 1014Ab, and thus the effect of reducing the electromagnetic noise can be enhanced. In addition, since it is only required to ground solder the grounding wire to the conductive portion 1015Aa and the conductive portion 1015Ab on the outer face, workability is better than in a case of soldering the grounding wire to the inner face. Furthermore, since the conductive portion 1015Aa and the conductive portion 1015Ab are provided on the outer face, it is possible to inspect whether the housing 101Aa and the housing 101Ab are grounded by a tester or the like from the outside of the housing 101Aa and the housing 101Ab, and thus workability is good.

Note that an insulating portion 1013Aa and an insulating portion 1013Ab may be provided in regions inside the insulating portion 1012Aa and the insulating portion 1012Ab on the outer faces of the housing 101Aa and the housing 101Ab to enhance the effect of preventing a current from flowing through a subject, or a conductive portion may be provided in these regions to enhance the effect of reducing the electromagnetic noise.

Third Embodiment

Figure 17:
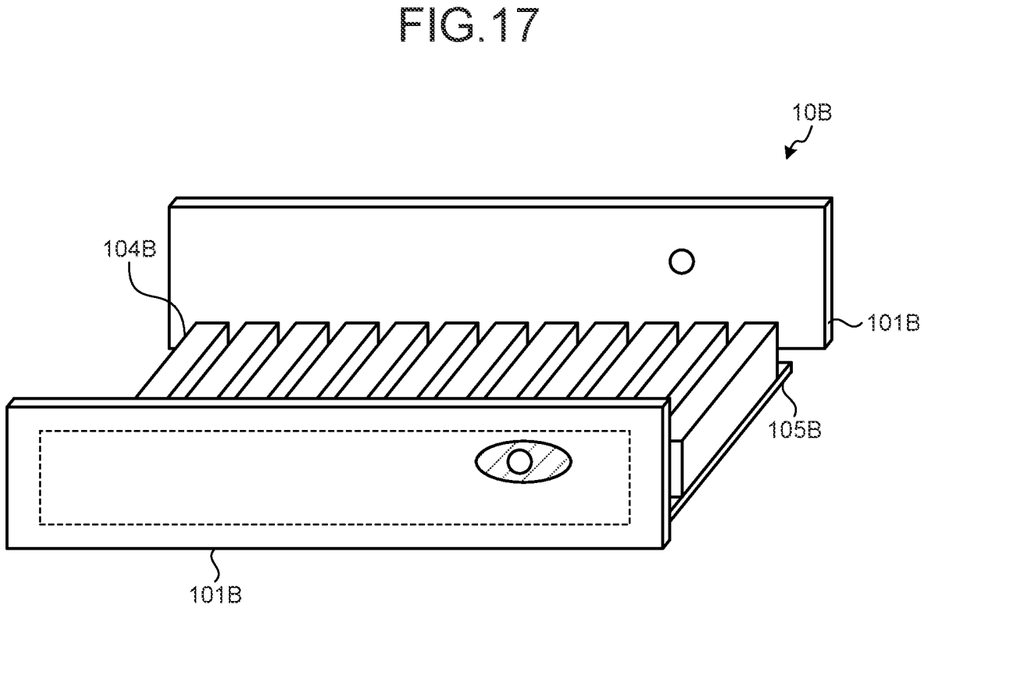
FIG. 17 is a schematic structure diagram of an ultrasound probe according to a third embodiment.

FIG. 17 is a schematic structure diagram of an ultrasound probe according to a third embodiment. FIG. 17 is an exploded perspective view of a part of an ultrasound probe 10B which is a linear-type ultrasound transducer. The ultrasound probe 10B includes a pair of housings 101B, a transducer array 104B in which a plurality of transducers that transmits and receives ultrasonic waves is arrayed with their longitudinal directions aligned, and an acoustic matching layer 105B that is positioned in a direction in which the individual transducers transmit ultrasonic waves and holds the transducers.

Figure 18:
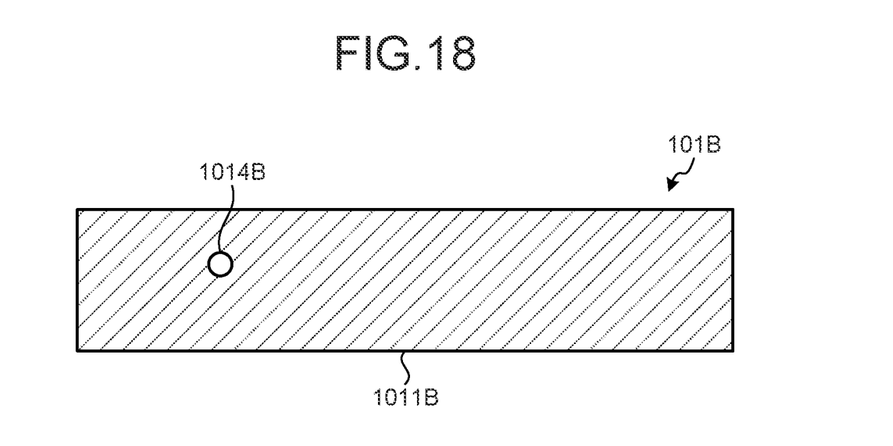
FIG. 18 is a diagram illustrating an inner face of a housing.

FIG. 18 is a diagram illustrating an inner face of a housing. As illustrated in FIG. 18, a housing 101B includes a conductive portion 1011B that has an electrical conductivity and that is provided over the entire inner face.

A through hole 1014B communicating from the inner face to the outer face is formed in the housing 101B. The housing 101B also includes a conductive portion that has an electrical conductivity and that is provided on an inner face of the through hole 1014B.

Figure 19:
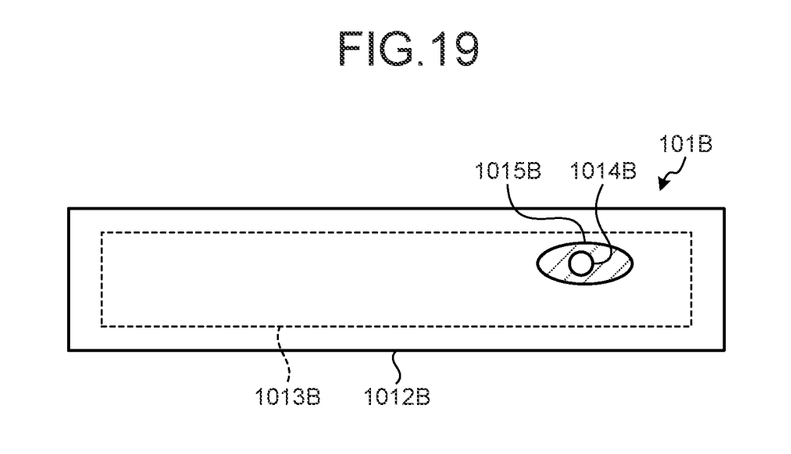
FIG. 19 is a diagram illustrating an outer face of the housing.

FIG. 19 is a diagram illustrating the outer face of the housing. As illustrated in FIG. 19, the housing 101B includes an insulating portion 1012B that has an insulating property and that is provided on the outer face. The insulating portion 1012B is provided at an outer edge portion including a region where the individual transducers are projected in the longitudinal direction. In addition, the housing 101B includes an elliptical conductive portion 1015B that has an electrical conductivity and that is provided around the through hole 1014B on the outer face.

According to the third embodiment described above, since the conductive portion 1011B is provided on the inner face of the housing 101B, the electromagnetic noise can be reduced. Furthermore, since the insulating portion 1012B is provided on the outer face of the housing 101B, even in a case where a large current flows due to lightning or the like, it is possible to prevent a current from flowing through a subject.

Furthermore, a grounding wire connected to a transducer is electrically connected to the conductive portion 1015B. As a result, the conductive portion 1011B on the inner face is grounded via the conductive portion of the through hole 1014B, and thus the effect of reducing the electromagnetic noise can be enhanced. In addition, since it is only required to solder the grounding wire to the conductive portion 1015B on the outer face, workability is better than a case where the grounding wire is soldered to the inner face. Furthermore, since the conductive portion 1015B is provided on the outer face, whether or not the housing 101B is grounded can be inspected from the outside of the housing 101B by a tester or the like, and thus workability is good.

Note that an insulating portion 1013B may be provided in a region inside the insulating portion 1012B on the outer face of the housing 101B to enhance the effect of preventing a current from flowing through a subject, or a conductive portion may be provided in this region to enhance the effect of reducing the electromagnetic noise.

Other Modifications

Figure 20:
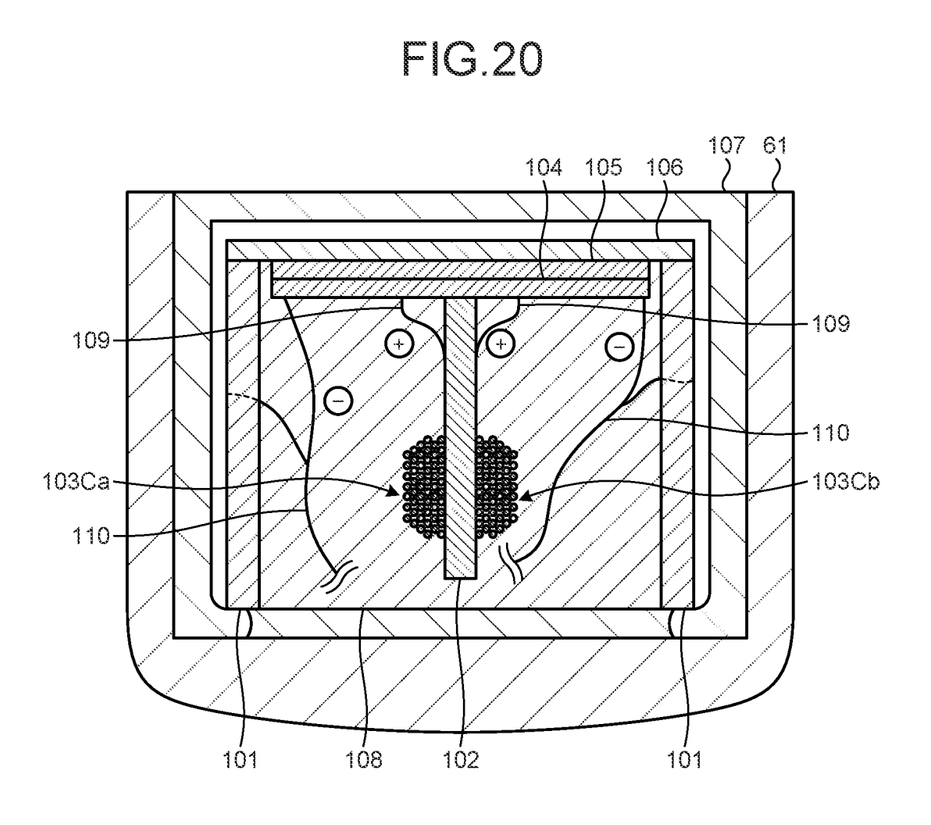
FIG. 20 is a cross-sectional view of the ultrasound probe.

FIG. 20 is a cross-sectional view of an ultrasound probe. FIG. 20 is a diagram illustrating the same cross section as that is FIG. 5, however, transducer cables 103Ca and 103Cb not illustrated in FIG. 5 are illustrated. Each transducer 1041 and one of the transducer cables 103Ca and 103Cb need to be connected in association with numbers corresponding to each other in order to control which transducer 1041 is caused to transmit what ultrasound pulse. The transducer cable 103Ca and the transducer cable 103Cb have different colors in the appearance. Cables with odd numbers are classified to be included in the transducer cable 103Ca, and the cables with even numbers are classified to be included in the transducer cable 103Cb. As a result, when connecting the individual transducers 1041 and the respective cables of the transducer cables 103Ca and 103Cb in association with numbers corresponding to each other, it is possible to facilitate the work of searching for a corresponding cable.

According to the disclosure, it is possible to implement an ultrasound probe, an ultrasound transducer unit, and an ultrasound endoscope that reduce electromagnetic noise and have high safety.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound probe comprising:
   a plurality of transducers arrayed with a longitudinal direction of each of the plurality of transducers aligned, each of the plurality of transducers having sides extending in the longitudinal direction and terminating at a pair of opposing ends; and
   a pair of housing plates configured to sandwich the plurality of transducers, each of the pair of housing plates extending in a plane perpendicular to the longitudinal direction, each of the housing plates including:
   a first material being electrically conductive, the first material provided on a first face adjacent to one of the pair of opposing ends of the plurality of transducers,
   a second material being electrically insulative, the second material provided on an outer edge of a second face opposing the first face, the outer edge including a region obtained by projecting each of the plurality of transducers on the second face in the longitudinal direction of each of the plurality of transducers,
   a third material being electrically conductive, the third material provided on the second face, and
   a fourth material configured to electrically connect the first material and the third material.

2. The ultrasound probe according to claim 1, further comprising:
   an acoustic matching layer positioned in a direction in which each of the plurality of transducers transmits ultrasonic waves, the acoustic matching layer facing each of the transducers,
   wherein the pair of housing plates are configured to hold first and second end sides, respectively, of the acoustic matching layer in the longitudinal direction.

3. The ultrasound probe according to claim 1, wherein the first material is disposed on a portion of the first face obtained by projecting each of the plurality of transducers on the first face in the longitudinal direction.

4. The ultrasound probe according to claim 3, wherein the first material is provided toward a center of the first face from the outer edge including the region, and the first material is disposed on an area of the first face that is half or more of an area of the first face.

5. The ultrasound probe according to claim 1, wherein each of the pair of housing plates include a portion that is electrically insulative and is provided at an outer edge of the first face.

6. The ultrasound probe according to claim 1, wherein each of the pair of housing plates include a portion that is electrically insulative and are provided on a side face connecting the first face and the second face.

7. The ultrasound probe according to claim 1,
wherein each of the pair of housing plates further comprising a through hole extending from the first face to the second face.

8. The ultrasound probe according to claim 7, wherein the fourth material is provided in the through hole.

9. The ultrasound probe according to claim 8, wherein the fourth material is provided on an inner face of the through hole.

10. The ultrasound probe according to claim 8, wherein the fourth material is a wiring inserted in the through hole.

11. The ultrasound probe according to claim 8, wherein the third material is located on the second material, the third material surrounds the through hole.

12. The ultrasound probe according to claim 11, wherein the second material is provided between the first material and the third material.

13. The ultrasound probe according to claim 1,
wherein each of the pair of housing plates include:
a semicircular portion having a semicircular shape, and
an extension portion having a side substantially coinciding with a diameter of the semicircular portion, the extension portion connecting two ends of an arc of the semicircular portion.

14. The ultrasound probe according to claim 1, wherein a grounding wire connected to the transducers is electrically connected to the first material.

15. An ultrasound endoscope comprising:
an ultrasound probe including:
a plurality of transducers arrayed with a longitudinal direction of each of the plurality of transducers aligned, each of the plurality of transducers having sides extending in the longitudinal direction and terminating at a pair of opposing ends; and
a pair of housing plates configured to sandwich the plurality of transducers, each of the pair of housing plates extending in a plane perpendicular to the longitudinal direction, each of the housing plates including:
a first material being electrically conductive, the first material provided on a first face each of adjacent to one of the pair of opposing ends of the plurality of transducers,
a second material being electrically insulative, the second material provided on an outer edge of a second face opposing the first face, the outer edge including a region obtained by projecting each of the plurality of transducers from the first face on the second face in the longitudinal direction of each of the plurality of transducers,
a third material being electrically conductive, the third material provided on the second face, and
a fourth material configured to electrically connect the first material and the third material; and
an insertion portion having a distal end provided with the ultrasound probe, the insertion portion being configured to be inserted into a subject.

16. The ultrasound endoscope according to claim 15, wherein each of the pair of housing plates further comprising a through hole extending from the first face to the second face.

17. The ultrasound endoscope according to claim 16, wherein the fourth material is provided in the through hole.

18. The ultrasound endoscope according to claim 17, wherein the third material is located on the second material, the third material surrounds the through hole.

19. The ultrasound endoscope according to claim 18, wherein the second material is provided between the first material and the third material.

20. The ultrasound endoscope according to claim 15, wherein each of the pair of housing plates include:
a semicircular portion having a semicircular shape, and
an extension portion having a side substantially coinciding with a diameter of the semicircular portion, the extension portion connecting two ends of an arc of the semicircular portion.

* * * * *